United States Patent [19]
Li

[11] Patent Number: 5,690,649
[45] Date of Patent: Nov. 25, 1997

[54] ANCHOR AND ANCHOR INSTALLATION TOOL AND METHOD

[75] Inventor: Lehmann K. Li, Milford, Conn.

[73] Assignee: Li Medical Technologies, Inc., Shelton, Conn.

[21] Appl. No.: 567,490

[22] Filed: Dec. 5, 1995

[51] Int. Cl.$^6$ .................................................. A61B 17/10
[52] U.S. Cl. .............................................. 606/139; 623/13
[58] Field of Search ................................ 606/139, 232, 606/60, 104, 72, 73, 75; 623/13; 411/2, 172, 174–176, 180, 188

[56] References Cited

U.S. PATENT DOCUMENTS

| | | |
|---|---|---|
| 34,293 | 6/1862 | Goble et al. . |
| 34,762 | 10/1862 | Goble et al. . |
| 1,247,621 | 11/1917 | Bennett . |
| 2,100,570 | 11/1937 | Saleh . |
| 2,143,086 | 1/1939 | Pleister . |
| 2,213,715 | 9/1940 | Monahan . |
| 2,453,056 | 11/1948 | Zack . |
| 2,562,419 | 4/1951 | Ferris . |
| 3,048,177 | 8/1962 | Takaro . |
| 3,155,095 | 11/1964 | Brown . |
| 3,254,650 | 6/1966 | Collito . |
| 4,011,602 | 3/1977 | Rybicki et al. . |
| 4,233,981 | 11/1980 | Schomacher . |
| 4,293,259 | 10/1981 | Liebig . |
| 4,447,915 | 5/1984 | Weber . |
| 4,454,612 | 6/1984 | McDaniel et al. . |
| 4,501,266 | 2/1985 | McDaniel . |
| 4,708,132 | 11/1987 | Silvestrini . |
| 4,738,255 | 4/1988 | Goble et al. . |
| 4,744,793 | 5/1988 | Pavr et al. . |
| 4,747,407 | 5/1988 | Liu et al. . |
| 4,759,765 | 7/1988 | Van Kampen . |
| 4,772,286 | 9/1988 | Goble et al. . |
| 4,776,330 | 10/1988 | Chapman et al. . |
| 4,870,957 | 10/1989 | Goble et al. . |
| 4,875,474 | 10/1989 | Border . |
| 4,892,547 | 1/1990 | Brown . |
| 4,898,156 | 2/1990 | Gatturna . |
| 4,899,743 | 2/1990 | Nicholson et al. . |
| 4,901,711 | 2/1990 | Goble et al. . |
| 4,911,153 | 3/1990 | Border . |
| 4,927,421 | 5/1990 | Goble et al. . |

(List continued on next page.)

FOREIGN PATENT DOCUMENTS

| | | |
|---|---|---|
| 0270704 | 6/1988 | European Pat. Off. . |
| 1368021 | 6/1964 | France . |
| 2622430 | 5/1989 | France . |
| 0343992 | 3/1931 | United Kingdom . |
| 9204874 | 4/1992 | WIPO . |

Primary Examiner—Michael Buiz
Assistant Examiner—Tina T. D. Pham
Attorney, Agent, or Firm—Ostrolenk, Faber, Gerb & Soffen, LLP

[57] ABSTRACT

Apparatus for inserting an anchor into a bore in a medium, the anchor being adapted to engage the walls of the bore for securing the anchor into the medium. The bore is sized slightly larger than the outside diameter of the anchor in its undeployed condition. The apparatus includes a first manually graspable member having a distal end and a proximal end, the distal end being adapted to releasably receive the anchor. The manually graspable member has a central opening therethrough, the proximal end of the manually graspable member having a pivotable handle extending therefrom. A second member is movable longitudinally in the central opening and is attached to the pivotable handle and to the anchor. A release member couples the anchor to the second member. The pivotable handle is pivotable with respect to the first member and exerts a force longitudinally on the second member to move the second member longitudinally in the first member. This movement exerts a force on the anchor connected thereto to deform the anchor to cause the anchor to engage the walls of the medium thereby to secure the anchor in the medium. The force exerted on the second member further acts on the release member to separate the anchor from the second member when the anchor has deformed to engage the walls of the bore.

65 Claims, 10 Drawing Sheets

U.S. PATENT DOCUMENTS

| | | |
|---|---|---|
| 4,946,468 | 8/1990 | Li . |
| 4,959,071 | 9/1990 | Brown et al. . |
| 4,960,420 | 10/1990 | Goble et al. . |
| 4,968,315 | 11/1990 | Gatturna . |
| 4,985,032 | 1/1991 | Goble . |
| 4,986,263 | 1/1991 | Dickerson et al. . |
| 4,997,433 | 3/1991 | Goble et al. . |
| 5,002,550 | 3/1991 | Li . |
| 5,002,574 | 3/1991 | May et al. . |
| 5,011,473 | 4/1991 | Gatturna . |
| 5,013,316 | 5/1991 | Goble et al. . |
| 5,019,105 | 5/1991 | Wiley . |
| 5,037,422 | 8/1991 | Hayhurst . |
| 5,037,426 | 8/1991 | Goble et al. . |
| 5,046,513 | 9/1991 | Gatturna . |
| 5,078,730 | 1/1992 | Li . |
| 5,084,058 | 1/1992 | Li . |
| 5,087,263 | 2/1992 | Li . |
| 5,092,891 | 3/1992 | Kummer et al. . |
| 5,094,563 | 3/1992 | Carletti . |
| 5,129,902 | 7/1992 | Goble et al. . |
| 5,133,723 | 7/1992 | Li et al. . |
| 5,141,520 | 8/1992 | Goble et al. . |
| 5,147,362 | 9/1992 | Goble . |
| 5,152,764 | 10/1992 | Goble . |
| 5,161,916 | 11/1992 | White et al. . |
| 5,163,946 | 11/1992 | Li . |
| 5,174,087 | 12/1992 | Bruno . |
| 5,176,682 | 1/1993 | Chow . |
| 5,192,303 | 3/1993 | Gatturna et al. . |
| 5,203,787 | 4/1993 | Noblitt et al. . |
| 5,207,679 | 5/1993 | Li . |
| 5,217,486 | 6/1993 | Rice et al. . |
| 5,250,058 | 10/1993 | Miller et al. . |
| 5,263,991 | 11/1993 | Wiley et al. . |
| 5,266,075 | 11/1993 | Clark et al. . |
| 5,268,001 | 12/1993 | Nicholson et al. . |
| 5,300,077 | 4/1994 | Howell . |
| 5,306,290 | 4/1994 | Martins et al. . |
| 5,312,416 | 5/1994 | Spaeth et al. . |
| 5,312,422 | 5/1994 | Trott . |
| 5,312,438 | 5/1994 | Johnson . |
| 5,313,962 | 5/1994 | Obenchain . |
| 5,314,427 | 5/1994 | Goble et al. . |
| 5,314,429 | 5/1994 | Goble . |
| 5,314,433 | 5/1994 | Li . |
| 5,318,577 | 6/1994 | Li . |
| 5,324,308 | 6/1994 | Pierce ............... 606/232 |
| 5,330,534 | 7/1994 | Herrington et al. . |
| 5,342,366 | 8/1994 | Whiteside et al. . |
| 5,350,380 | 9/1994 | Goble et al. . |
| 5,354,298 | 10/1994 | Lee et al. . |
| 5,354,300 | 10/1994 | Goble et al. . |
| 5,356,413 | 10/1994 | Martins et al. . |
| 5,358,511 | 10/1994 | Gatturna et al. . |
| 5,372,599 | 12/1994 | Martins . |
| 5,372,604 | 12/1994 | Trott . |
| 5,376,120 | 12/1994 | Sarver et al. . |
| 5,393,302 | 2/1995 | Clark et al. . |
| 5,443,482 | 8/1995 | Stone et al. ............... 606/232 |
| 5,464,425 | 11/1995 | Skiba . |
| 5,464,427 | 11/1995 | Curtis et al. . |
| 5,486,197 | 1/1996 | Le et al. ............... 606/232 |
| 5,531,792 | 7/1996 | Huene ............... 623/16 |
| 5,534,004 | 7/1996 | Santangelo . |
| 5,545,180 | 8/1996 | Le et al. ............... 606/232 |

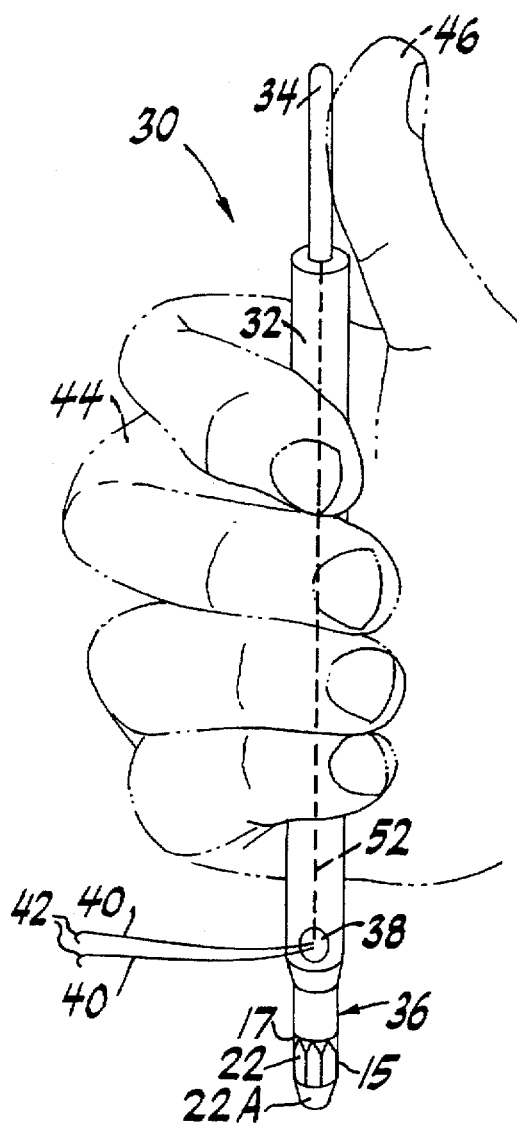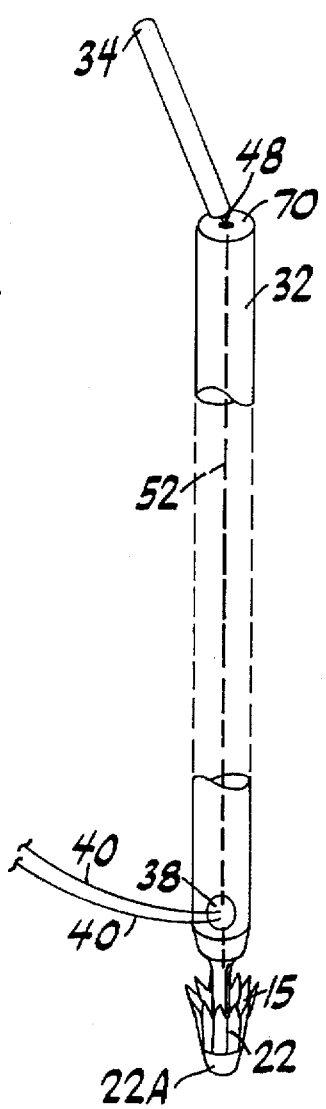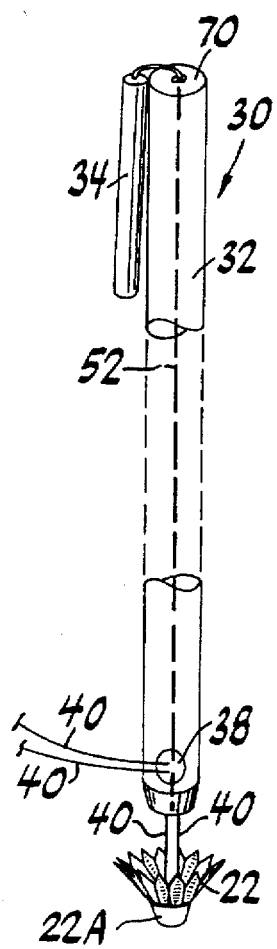

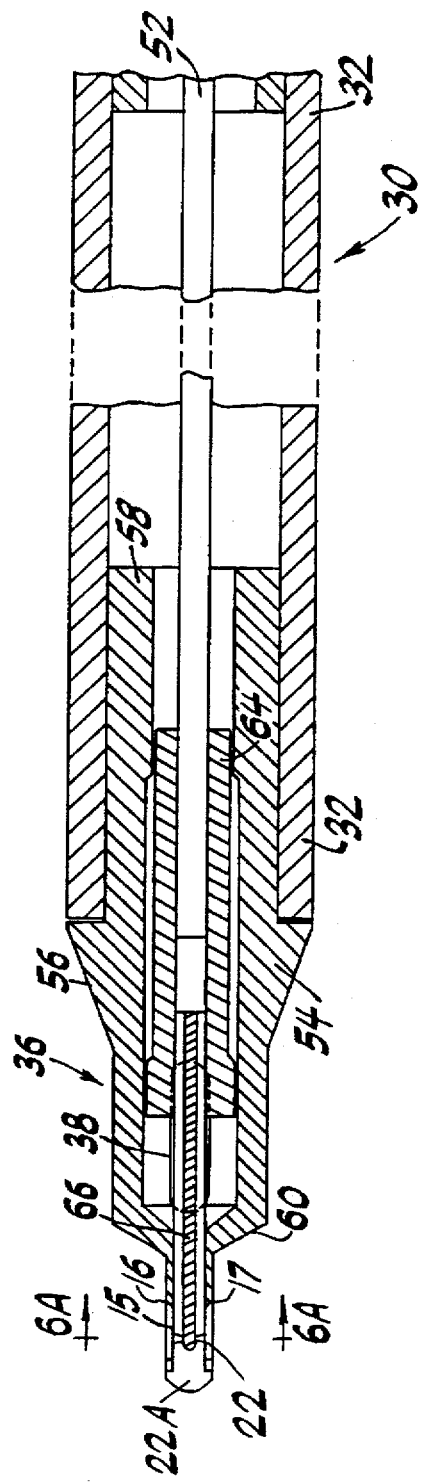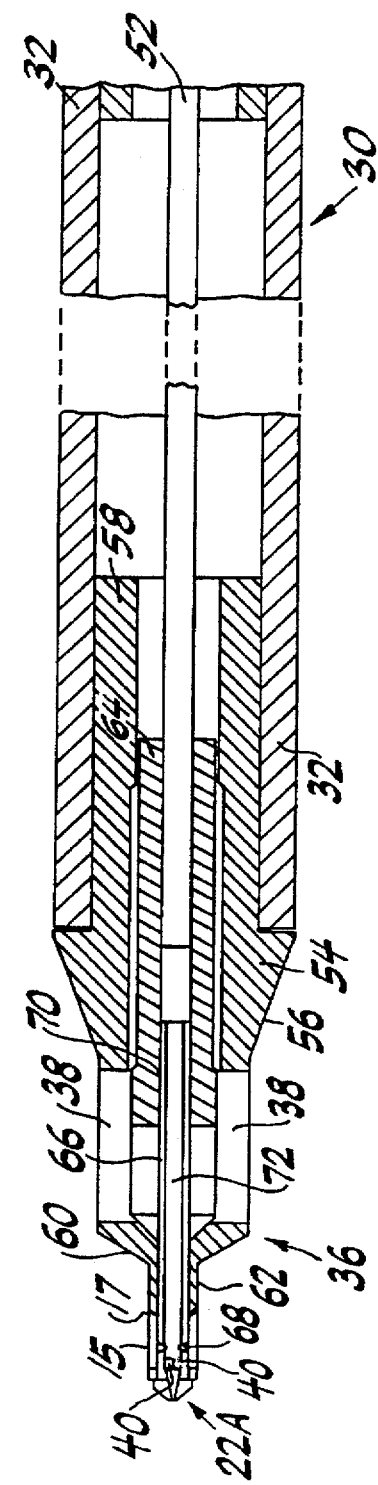
FIG. 6
FIG. 7

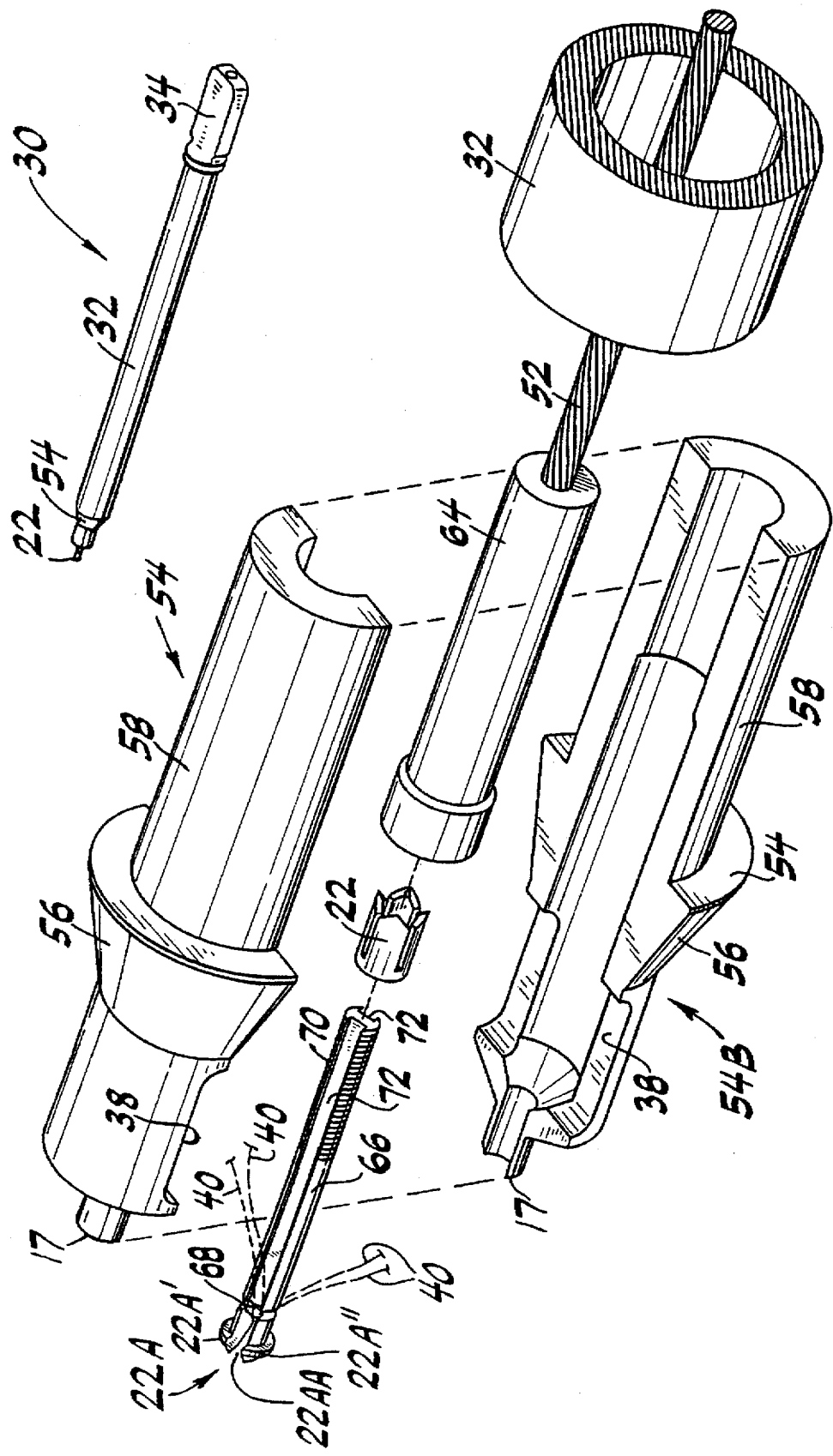

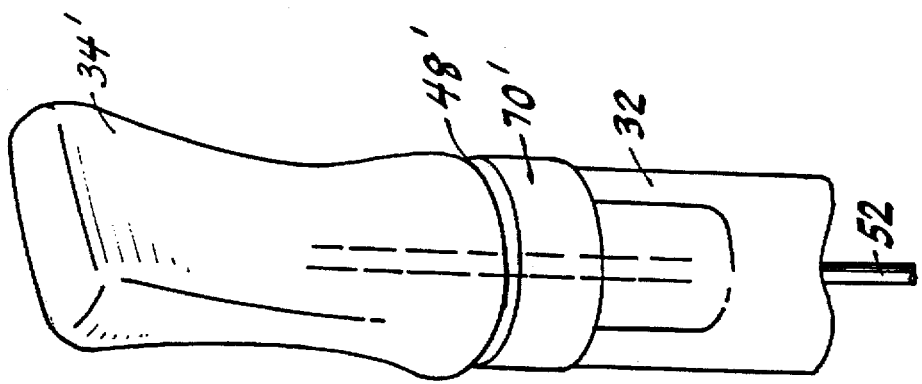
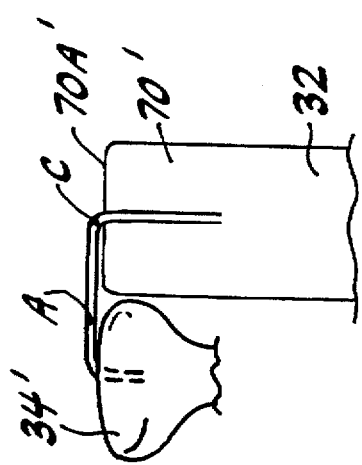
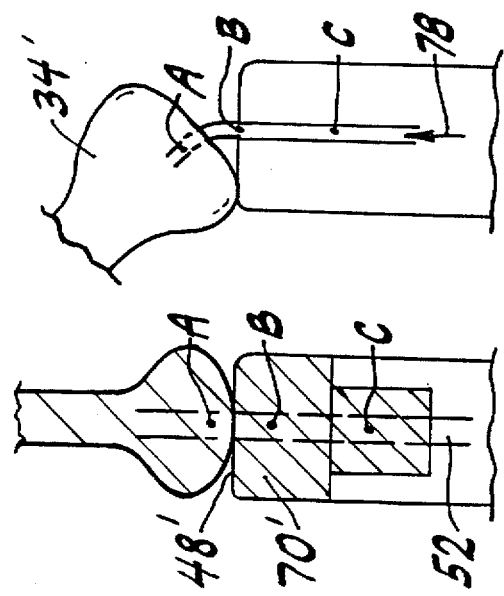

ANCHOR AND ANCHOR INSTALLATION TOOL AND METHOD

BACKGROUND OF THE INVENTION

The present invention relates to anchors for fastening one component to another component, and in particular, to a medical anchor implantable in organic tissue. Even more particularly, the present invention relates to a suture anchor which can be implanted into organic tissue, for example bone, to anchor a suture in the bone. The invention also relates to an instrument for inserting the anchor as well as a method for inserting the anchor, particularly into organic tissue. Although the present invention is described as a suture anchor, the invention also is suitable as an anchor for anchoring other devices, for example prostheses. Furthermore, the invention is not limited to the surgical or medical field, and can be used to implant anchors into media other than tissue, e.g., into wood or plastic.

Examples of two prior art anchors include the device described in U.S. Pat. No. 5,002,550 and the anchor described in U.S. Pat. No. 5,141,520.

In both of these references, a suture anchor is described. In U.S. Pat. No. 5,002,550, a suture anchor and installation tool are described. The suture anchor has a curved barb which is flexed upon insertion into a bore and which engages the wall of the bore to maintain the anchor in position. In U.S. Pat. No. 5,141,520, a harpoon type of suture anchor is described which is driven into the bone by a hammer force.

In both devices of the prior art, the suture anchors must be forcibly driven into a bore provided in bone, for example. In the device in the '550 patent, a flexible barb must be deformed as it is inserted into the bore, and in the device of the '520 patent, the anchor has surfaces disposed on its periphery which wedge the anchor into the bone. Accordingly, in both of these types of anchors, there is the possibility of damage to the material in which the anchor is being inserted due to the force which is exerted in implanting the anchor.

In addition, in both of the references, the anchors disclosed are not fixedly attached to the insertion tool which is provided for inserting the anchor into the organic tissue. Accordingly, the anchors can fall off the distal ends of the insertion devices. Therefore, in both of these references, the anchor is not fully stabilized during the implantation process and may become misaligned or completely fall off the distal end of the insertion tool.

SUMMARY OF THE INVENTION

It is, therefore, an object of the present invention to provide an anchor, particularly a suture anchor, which overcomes the described problems of the prior art.

It is yet still a further object of the present invention to provide an anchor which allows for the placement of the anchor with high accuracy.

It is yet still a further object of the present invention to provide an anchor which can be implanted into organic tissue and which is easily implanted without the risk of misalignment or disconnection from the insertion tool.

It is yet still a further object of the present invention to provide an insertion tool for the described anchor.

It is yet still a further object of the present invention to provide an insertion tool which allows for convenient and simple insertion of an anchor into organic tissue.

It is yet still a further object of the present invention to provide an insertion tool and anchor which prevents damage to the tissue in which the anchor is being inserted during the installation procedure.

It is yet still a further object of the present invention to provide a pre-packaged anchor and anchor insertion tool, and particularly an anchor and insertion tool which is adapted for a single use, the insertion tool being thereafter disposable.

It is yet still a further object of the present invention to provide an insertion tool which is inexpensive to manufacture and accordingly, economically used in a disposable fashion.

The above and other objects of the present invention are achieved by an apparatus for inserting an anchor into a bore in a medium, the anchor being adapted to engage the walls of the bore for securing the anchor into the medium, the apparatus comprising: a first manually graspable member having a distal end and a proximal end, the distal end being adapted to releasably receive the anchor, said manually graspable member having a central opening therethrough, the proximal end of the manually graspable member having a pivotable handle extending therefrom; a second member movable longitudinally in the central opening attached to said pivotable handle and to said anchor; a release member releasably coupling said anchor to said second member; said pivotable handle being pivotable with respect to said first member and exerting a force longitudinally on said second member to move said second member longitudinally in said first member and exert a force on said anchor connected thereto to deform said anchor to cause said anchor to engage the walls of the medium thereby to secure the anchor in the medium; said force exerted on said second member further acting on said release member to separate said anchor from said second member when said anchor has deformed to engage the walls of the bore.

The above and other objects of the present invention are also achieved by a method of securing an anchor into a bore in a medium, the anchor being adapted to engage the walls of the bore for securing the anchor into the medium, the method comprising: inserting an anchor held to a distal end of an insertion tool into the bore; applying a force to a lever extending from the insertion tool to cause a force to be exerted on the anchor by a coupling member to deform the anchor into engagement with the walls of the bore in the medium and separating the anchor from the coupling member; and pulling the insertion tool away from the anchor leaving the anchor secured in the bore in the medium.

The above and other objects of the invention are furthermore achieved by apparatus for inserting an anchor into a bore in a medium, the anchor being adapted to engage the walls of the bore for securing the anchor into the medium, the apparatus comprising: an anchor comprising at least one hollow cylindrical section having one of proximally or distally extending fingers adapted to be deformed radially outwardly to engage the walls of the bore to secure the anchor in the medium; a first manually graspable member having a distal end and a proximal end, the distal end releasably receiving the anchor, said manually graspable member having a central opening therethrough, the proximal end of the manually graspable member having a pivotable handle extending therefrom; a second member movable longitudinally in the central opening attached to said pivotable handle and to said anchor; a release member releasably coupling said anchor to said second member; said pivotable handle being pivotable with respect to said first member and exerting a force longitudinally on said second member to move said second member longitudinally in said first member and exert a force on said anchor connected thereto to deform said anchor to cause said anchor to engage the walls of the medium thereby to secure the anchor in the medium; and said force exerted on said second member further acting on said release member to separate said anchor from said second member when said anchor has deformed to engage the walls of the bore.

The above and other objects of the invention are additionally achieved by an anchor for implantation in a bore in a medium, the anchor comprising: a cylindrical hollow section having a plurality of longitudinally extending fingers for outward radial movement for engaging the walls of the bore in response to a force applied to the anchor by an insertion tool causing the fingers to move against a cam surface; and a central longitudinally extending member extending through the hollow section and having a shoulder at a distal end preventing movement proximally past the hollow section, the central member having a shaft for engagement by the insertion tool, said central member including a releasable connection for separating a distal portion of the central member from a proximal portion of the central member coupled to the insertion tool.

Other objects, features and advantages of the present invention will become apparent from the following description of the invention which refers to the accompanying drawings.

BRIEF DESCRIPTION OF THE DRAWINGS

The invention will now be described in greater detail in the following detailed description with reference to the drawings, in which:

FIG. 1 shows the anchor and anchor insertion tool according to the present invention in perspective view in use;

FIG. 2 shows the anchor and anchor insertion tool of FIG. 1 during the initial deployment of the anchor;

FIG. 3 shows the anchor and anchor insertion tool once the anchor has been fully deployed;

FIG. 6 is a longitudinal cross section of the anchor and anchor insertion tool according to the present invention prior to deployment;

FIG. 7 is a longitudinal cross section showing the anchor and anchor insertion tool after sutures have been threaded into the anchor during manufacture and the distal tip of the anchor crimped to prevent the suture from coming out of the anchor at the distal end;

FIG. 10 shows the insertion tool with anchor attached in a perspective view;

FIG. 11 is an exploded view of the anchor and distal end of the insertion tool;

FIG. 17 is a longitudinal cross section showing another embodiment of the proximal end of the insertion tool, showing a different embodiment of the handle employed for actuating the anchor;

FIG. 18 is a longitudinal cross section showing a first step during the securement of the anchor according to the device shown in FIG. 17;

FIG. 19 is a longitudinal cross section showing a further first step in the securement of the anchor having a handle according to FIG. 17;

FIG. 20 shows the embodiment of the proximal end of the insertion tool, shown in FIG. 17, in perspective view;

DETAILED DESCRIPTION OF THE DRAWINGS

Figure 5:
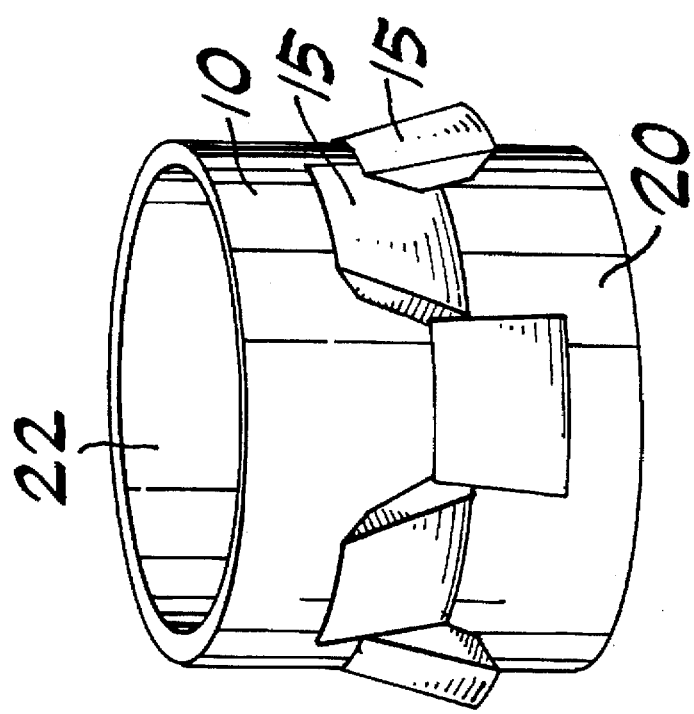
FIG. 5 shows the anchor and anchor insertion tool of FIG. 4 with the anchor in its deployed position.
Figure 4:
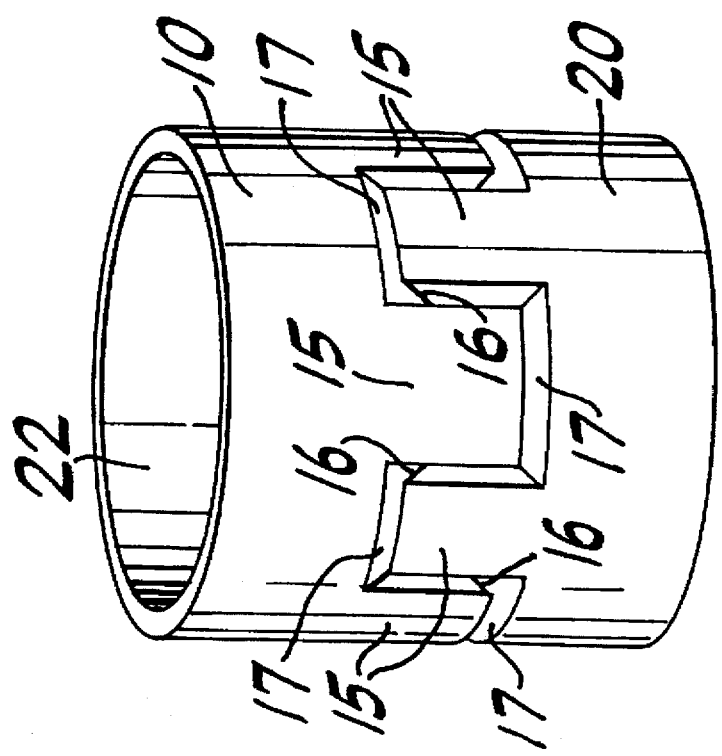
FIG. 4 schematically shows, in perspective view, an embodiment of an anchor employed with the insertion tool according to the present invention.
Figure 6A:
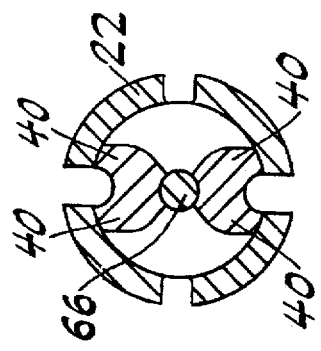
FIG. 6A is a cross section of the device shown in FIG. 6 along lines 6A—6A.
Figure 21A:
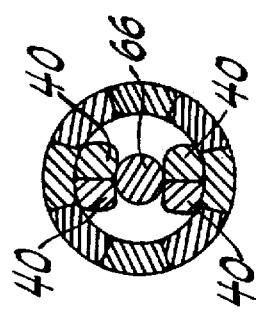
FIG. 21A is a cross section taken along lines 21A—21A of FIG. 21.
Figure 6B:
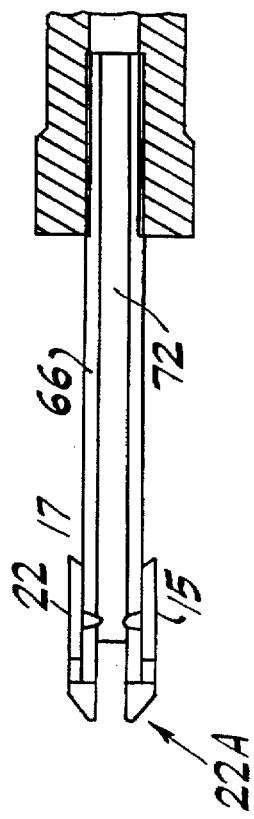
FIG. 6B is a longitudinal cross section showing the anchor and a portion of the anchor insertion tool in a cross sectional view rotated by 90° from the view shown in FIG. 6.
Figure 22:
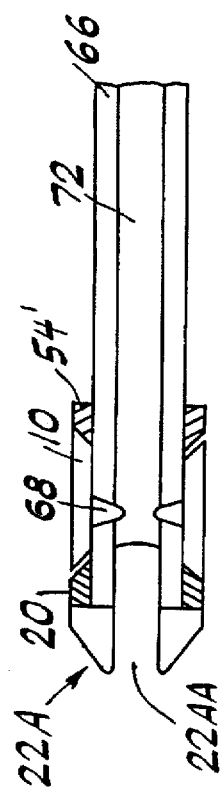
FIG. 22 is a longitudinal cross sectional view through the anchor shown in FIG. 21.
Figure 23:
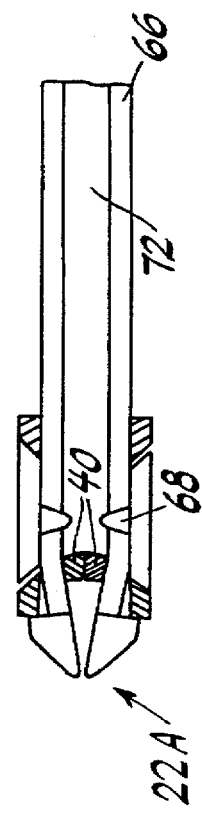
FIG. 23 is a longitudinal cross section showing the anchor of FIG. 22 rotated by 90° and also showing the sutures threaded through the anchor with the tips of the anchor crimped during the manufacturing process.

With reference now to the drawings, FIGS. 1, 2 and 3 show one embodiment of the anchor installation tool according to the present invention in perspective view and showing the insertion tool during progressive steps in deployment of a surgical anchor. The surgical anchor employed in the present invention is a modification of the surgical anchor described in detail in applicant's co-pending U.S. application Ser. No. 08/294,407 filed Aug. 22, 1994. An example of such an anchor is shown in FIGS. 4 and 5. The anchor shown in FIGS. 1, 2 and 3 is similar to the anchor shown in FIGS. 4 and 5. However, the anchor shown in FIGS. 1, 2 and 3 is of the type having fingers 15 which extend only proximally. The anchor shown in FIGS. 4 and 5 has fingers 15 which extend both proximally and distally.

The installation tool according to the present invention can be used with anchors of the type shown in FIGS. 4 and 5 and also with anchors having fingers 15 extending only proximally or only distally, i.e., anchors having only a portion 10 or 20 with fingers extending only proximally or only distally.

As shown in FIGS. 4 and 5, an anchor insertable into a bore in organic tissue, for example a bore drilled in bone, may comprise two sections 10 and 20. Section 20 includes proximally extending fingers 15 and section 10 includes distally extending fingers 15. The fingers are interdigitated in this embodiment. The fingers 15 of the anchor 22 include chamfered edges 16 which are adapted to engage with corresponding opposed chamfered surfaces 17 of the opposed section. When the two sections 10 and 20 are moved relatively toward each other, the opposed chamfered surfaces 16 and 17 force the fingers 15 radially outwardly, as shown in FIG. 5, causing the fingers to engage in the bore drilled in the organic tissue, thereby fixing the anchors in the organic tissue.

As described above, the anchor may include only a single section 10 or 20 having only proximally extending fingers 15. In such a case, the anchor is moved against a surface of the installation tool, as will be described in greater detail herein, causing the fingers to move outwardly and to engage the wall of the bore, thereby preventing the anchor from being pulled out of the bore.

As shown in FIG. 1, the device according to the present invention comprises an insertion tool generally designated 30. The insertion tool includes a cylindrical hollow body portion 32, a pivotable handle actuating portion 34 and a distal portion 36 for supporting and forming the anchor 22. The member 32 need not be cylindrical, it can take any other convenient, ergonomic form. In FIG. 1, the anchor is shown prior to formation. The anchor includes a plurality of proximally extending fingers 15. In FIG. 2, the anchor 22 is shown after the plurality of fingers 15 have been moved radially outwardly to allow the fingers to engage in a bore in organic tissue.

The hollow member 32 includes at least one, and preferably two, openings or windows 38 at its distal end through which sutures 40, with any suitable surgical needles 42 attached, extend. If two openings 38 are provided, they are located on opposed surface of member 32. As explained herein in greater detail, the anchor 22 also includes a central tip portion 22A, not shown in FIGS. 4 and 5, but shown in the other figures, the purpose for which will be explained in greater detail below.

As shown in FIGS. 1, 2 and 3, the insertion tool is grasped as shown by the user's fingers 44. The user's thumb 46 is placed against the handle actuating portion 34 and the anchor 22 is inserted into the opening, not shown, in the organic tissue. It will be noted that because the fingers 15 do not extend outwardly initially beyond the diameter of the anchor 22 and the diameter of the bore is sized to be only slightly larger than the diameter of the undeployed anchor, the anchor can be inserted very easily, without applying any force to the organic tissue. Thus, unlike the prior art, the organic tissue cannot be damaged during the insertion process. Once the anchor has been inserted into the bore in the organic tissue, the operator applies a transverse force to the handle 34, pivoting the handle 34, which is preferably coupled to the cylindrical portion 32 via frangible connection 48, causing the distal portion of the handle 34 to pivot and cam against the surface of portion 70 of the cylindrical portion 32. As will be explained in greater detail below, the handle portion 34 is coupled to the anchor 22 via a flexible connection, for example a cable or wire 52, causing a force to be transmitted to anchor 22 when handle 34 pivots. This causes the anchor 22 to be moved against a chamfered surface 17 of the installation tool at the distal end, thereby forming the anchor 22 into engaging position as shown in FIG. 2. The fingers 15 of the anchor thereby move outwardly to cause the anchor to engage the walls of the bore in the organic tissue.

Upon further pivoting of the handle portion 34 into the position shown approximately in FIG. 3, a frangible connection at the distal end, to be shown in greater detail below, connecting the anchor 22 itself to a member connected to the wire 52, breaks, thereby disconnecting the insertion tool from the anchor, leaving the anchor, with the sutures 40 attached thereto, deployed in the organic tissue. The sutures 40 extend through openings 38 in the tool and can be retracted through the opening 38 to allow the insertion tool 30 to be separated from the sutures. The anchor 22 with sutures attached is thereby left in the bore ready for the connection to another component, for example a prosthesis or other organic tissue.

FIGS. 6–9 show an embodiment of the insertion tool according to the present invention used to implant an anchor having only proximally extending fingers 15. The insertion tool 30 includes a hollow cylindrical member 32, through which extends a flexible element, for example a cable or wire 52. The cylindrical element 32 receives at its distal anchor-supporting end 36, an insert 54 having a frustoconically shaped surface 56. The insert 54 has a cylindrical proximally extending portion 58 adapted to be received in the hollow bore of the cylindrical member 32. The insert 54 tapers again at its distal end at a portion 60, terminating in a terminal portion 62 having a chamfered surface 17 adapted to engage the chamfered surfaces 16 of fingers 15, thereby to form fingers 15 outwardly when the anchor 22 moves toward the chamfered surface 17 of the insert 54. As best shown in FIG. 11, insert 54 comprises two half sections 54A and 54B.

Flexible element 52 is fixedly attached to a coupling member 64, as shown more clearly in FIG. 11. The anchor 22, for example as shown in FIG. 11, of the type having only proximally extending fingers (but which could have both proximally and distally extending fingers as shown in FIGS. 4 and 5), is slidably received on a threaded shaft 66, which is preferably integrally coupled to tip portion 22A. Tip portion 22A is releasably coupled to threaded shaft 66, preferably via a frangible connection 68 comprising a portion of shaft 66 of reduced cross section, e.g., a slit or score line causing the shaft to have reduced tensile strength at this point.

Coupling member 64 includes internal threads which receive threads 70 of the threaded shaft 66, thereby capturing anchor 22 between the shoulder of forked tip 22A and chamfered tip portions 17 of portions 54A and 54B of insert 54.

Threaded shaft 66 includes longitudinally extending slots 72 on opposed sides thereof, through which sutures 40 can be longitudinally received, at least in part. The sutures 40 thereafter extend through the windows 38 formed in the two half portions designated 54A and 54B of the insert 54.

As shown in FIG. 11, during the assembly process, the sutures 40 are threaded into a slot 22AA provided in the forked tip 22A. One or a plurality of sutures may be threaded through the slot 22AA in such a way that the suture is looped around the base portion of the slot 22AA, and thence extending longitudinally along a portion of the slots 72 in the threaded shaft 66. The respective ends of the sutures 40 thereafter extend through the openings 38 in the insert 54.

Figure 8:
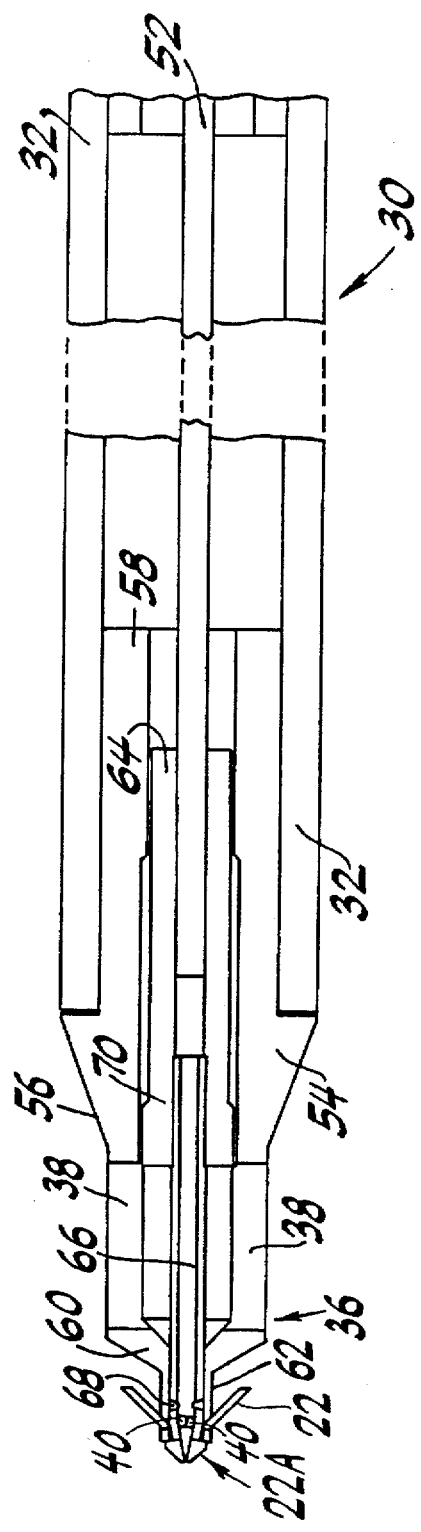
FIG. 8 is a longitudinal cross section showing the anchor and anchor insertion tool after the anchor has been deployed but prior to removal of the insertion tool from the anchor.
Figure 9:
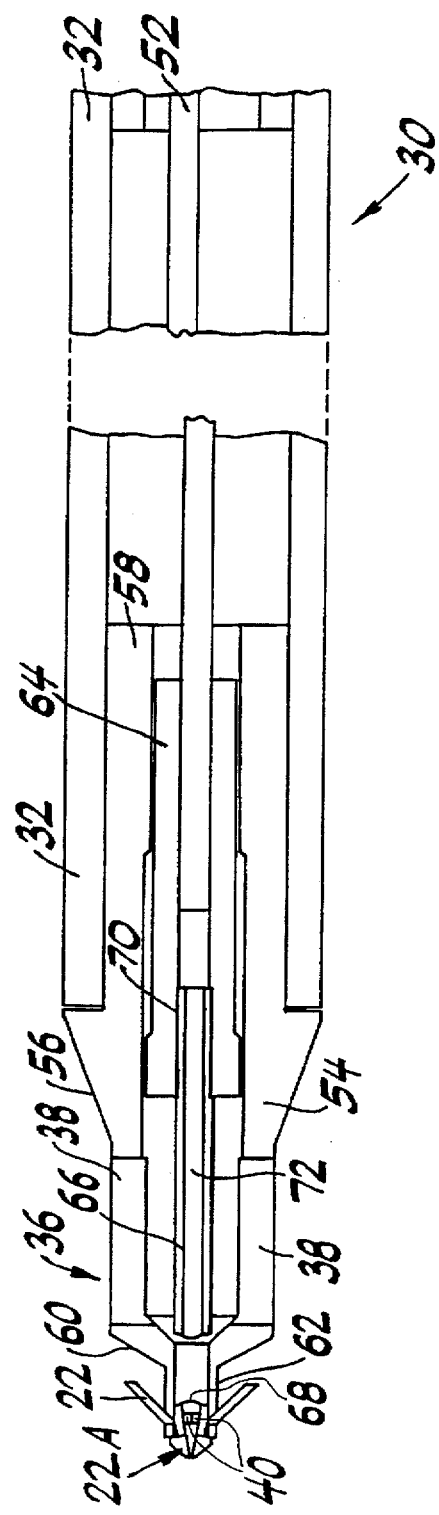
FIG. 9 is a longitudinal cross section showing the anchor and anchor insertion tool after the anchor has become detached from the actuating portion of the insertion tool and just prior to removal of the insertion tool from the anchor.
Figure 12:
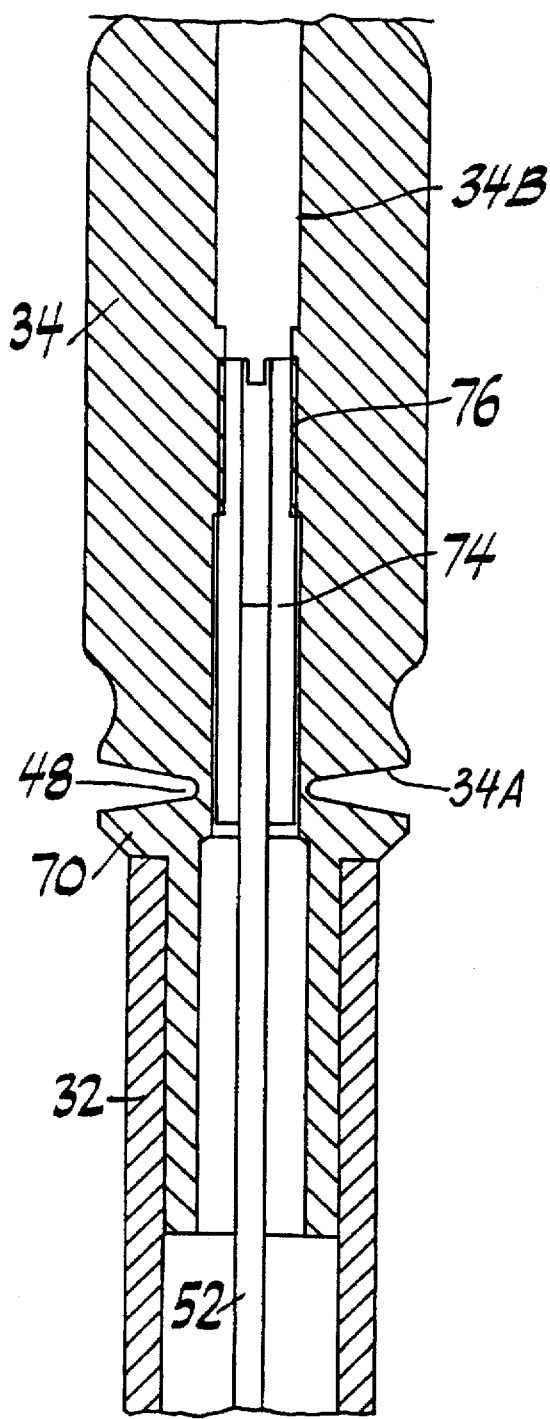
FIG. 12 is a longitudinal cross section showing the proximal end of the insertion tool, showing the actuating handle.
Figure 13:
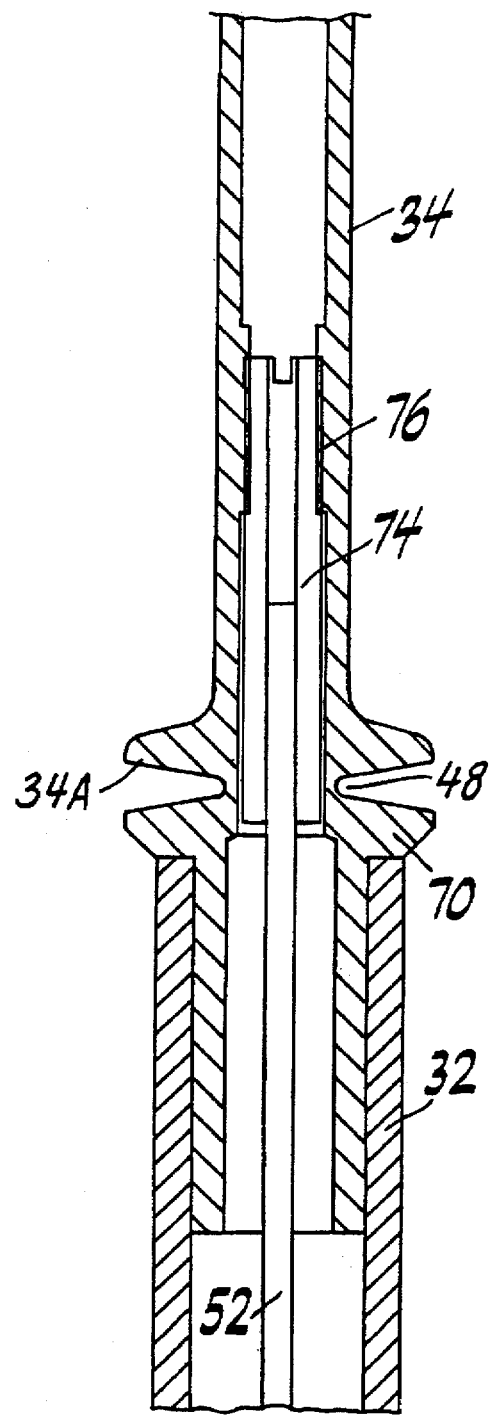
FIG. 13 is a longitudinal cross section showing the proximal end of the insertion tool rotated 90° with respect to that shown in FIG. 12.

Once the sutures 40 have been inserted into the slot 22AA, the two opposed portions 22A' and 22A" are crimped together, as shown in FIGS. 7, 8 and 9. This secures the sutures in position and prevents them from slipping out of the slot 22AA in the tip 22A. The anchor assembly 22 with shaft 66 is threaded into coupling member 64 and insert 54 halves 54A and 54B are assembled to maintain the assembly together. During assembly, the ends of sutures 40 are threaded through the openings 38.

FIGS. 12–16 show the proximal end of the insertion tool, according to one embodiment of the invention. The proximal end includes an actuating handle 34 which may be integrally connected to an insert portion 70 received within the bore of the proximal portion of cylindrical member 32. Handle 34 and portion 70 are releasably coupled, preferably by a frangible connection 48 comprising an area between handle 34 and portion 70 of reduced cross section and accordingly, reduced tensile strength. Wire for cable 52 is coupled to a proximal coupling element 74 which is threaded into an internal bore 34A in handle 34, as shown at 76.

Figure 16:
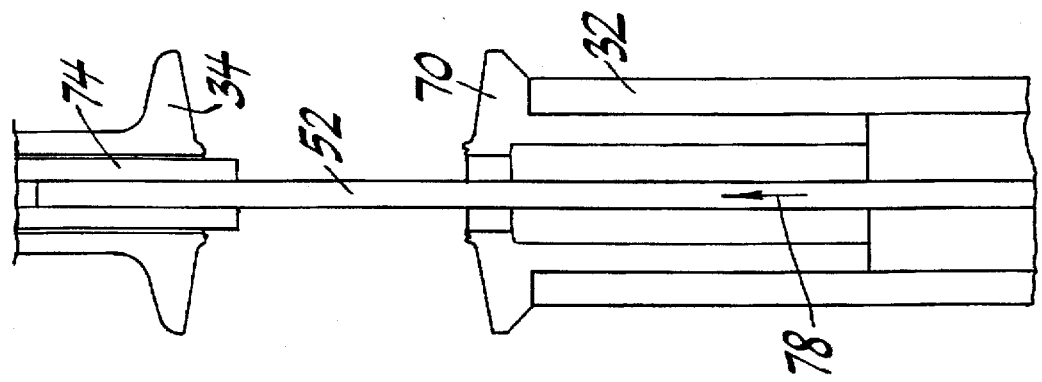
FIG. 16 is a longitudinal cross section showing yet a further step during the activation of the anchor when the actuating portion of the insertion tool has become detached from the anchor.
Figure 15:
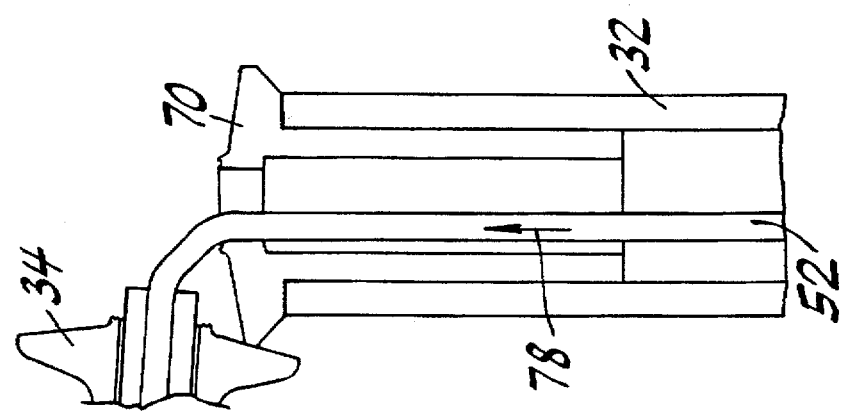
FIG. 15 is a longitudinal cross section showing a further step during the securement of the anchor.
Figure 14:
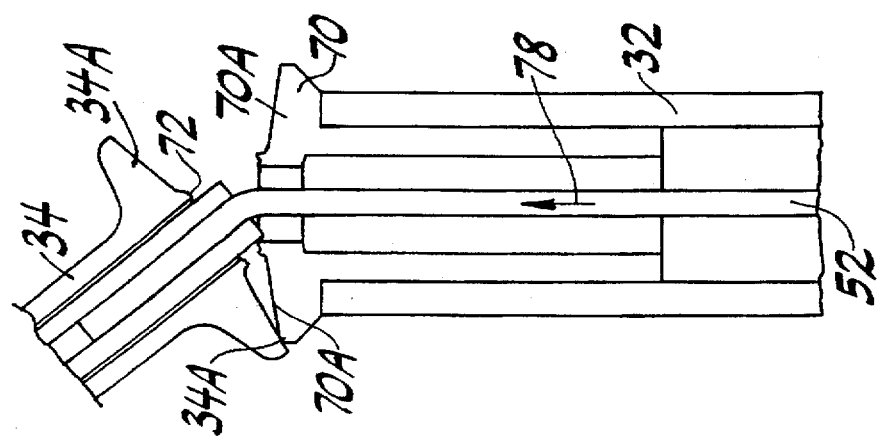
FIG. 14 is a longitudinal cross section showing a portion of the proximal end of the insertion tool, showing the initial step employed during securement of the anchor.
Figure 21:
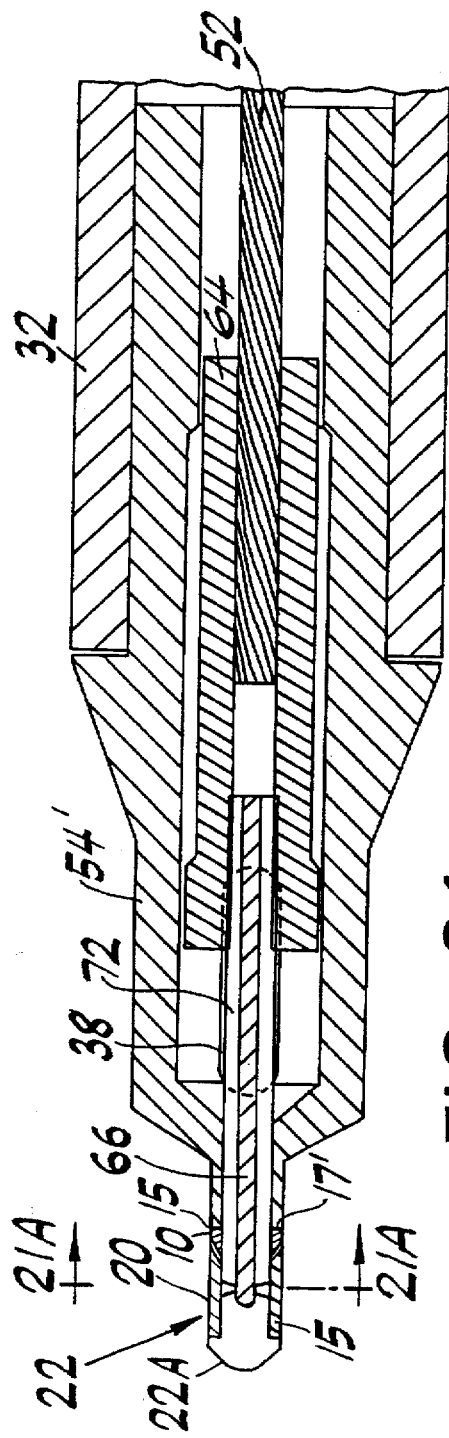
FIG. 21 is a longitudinal cross section showing the distal end of the insertion tool having an anchor of the type shown in FIGS. 4 and 5 having engaging fingers extending both proximally and distally.

As shown in FIG. 14 and with reference to FIGS. 6 to 9, to activate and deploy the anchor 22, the anchor 22, attached to the device 30 preferably during assembly of the tool, is inserted into the bore in the organic tissue, for example a bore in bone. The anchor 22 is inserted into the bore without applying any force to the organic tissue because the fingers 15 of the anchor 22 are undeployed i.e., in their unextended position. To deploy the anchor 22, the user applies a transverse force to handle 34, thus breaking the frangible connection 48 and pivoting the handle portion 34. The handle portion 34 has a distal portion 34A which is engageable with a proximal surface 70A of the portion 70. The pivoting cam action of the handle 34 causes a tension to be applied to the wire 52, causing it to move in the direction shown by the arrow 78. This causes the fingers 15 of the anchor 22 to move against the chamfered surface 17 of the insert 54 at the distal end of the insertion tool. After the frangible connection 48 at the distal end of the handle 34 breaks, the pivoting cam motion of the handle 34 is continued. As the wire 52 pulls the anchor 22 in the proximal direction, the fingers 15 move against surface 17 and begin to move radially outwardly, as shown in FIG. 8. The fingers 15 thus engage in a bore into which the anchor 22 has been inserted. Upon further pivoting of the handle 34, as shown in FIG. 15, the frangible connection 68 at the distal end of the insertion tool i.e., the frangible connection 68 connecting the tip portion 22A to the threaded shaft 66, breaks, thereby disconnecting the shaft 66 from the tip portion 22A of the anchor 22, leaving the handle 34 free, as shown in FIG. 16. The insertion tool 30 can now be withdrawn, leaving the anchor 22 with the tip portion 22A through which the sutures 40 are threaded in position in the bore in the organic tissue. At this point, the sutures 40 still extend through the openings 38 in the distal end of the insertion tool 30. By suitable threading of the sutures through the openings 38, the insertion tool 30 can be removed completely from the sutures. The suture anchor 22 with attached sutures is now fixed in position within the bore hole.

FIGS. 17–20 shown an alternative embodiment of the handle portion of the present invention. As shown in these figures, a handle 34' is provided suitably formed to provide a convenient surface for actuating by the hand of the user.

As in the embodiment shown in FIGS. 12–16, in the initial position, the wire 52 is relatively unstressed or has just enough tension to maintain the anchor 22 such that the chamfered surfaces 16 of the fingers 15 of the anchor 22 and the corresponding surface 17 of the member 54 are in engagement. To actuate the anchor 22, the user pivots the handle 34', breaking the frangible connection 48'. As shown, point A of the wire 52 moves to the position shown in FIG. 18. Points B and C move as shown. At some point, point B moves to the position illustratively shown, at which point the fingers 15 of the anchor 22 begin to deploy. Upon further pivoting of the handle 34', illustratively shown in FIG. 19 where point C has moved to the point adjacent the top surface 70A' of the member 70', the anchor is fully deployed and the frangible connection 68 coupling the anchor 22A to the threaded shaft 66 breaks, allowing the insertion tool to be removed from the anchor, leaving the anchor 22 in position in the bore hole.

Figure 24:
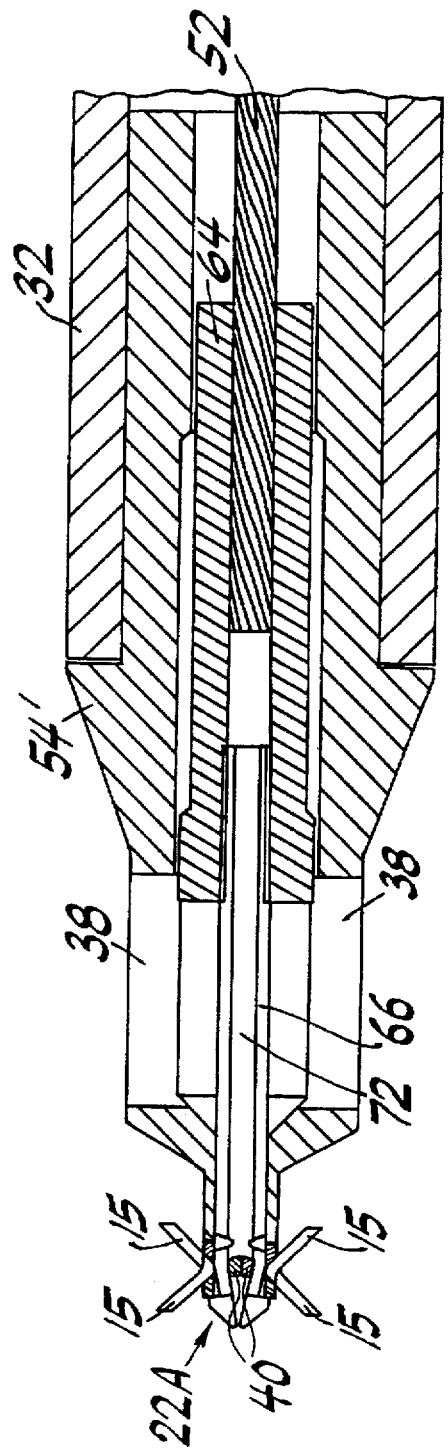
FIG. 24 is a longitudinal cross section showing the distal end of the anchor insertion tool and the anchor upon deployment of the anchor and just prior to separation of the anchor insertion tool from the anchor.

FIGS. 21, 21A and 22–24 show the distal end of the insertion tool according to the present invention wherein the anchor 22 comprises an anchor having proximally and distally extending fingers 15, as shown in FIGS. 4 and 5. In this embodiment, the distal tip of the member 54' is formed with a straight cut edge 17', thereby abutting one portion 10 of the anchor 22. The embodiment shown in these figures operates in the same way as in the other embodiments previously described. Tension in the wire 52 caused by pivoting of the handle 34 causes the member 20 to be moved against the member 10 of the anchor 22. Member 10 abuts surface 17', and thus is prevented from moving. The fingers 15 thus move into the positions shown in FIG. 24, thereby securing the anchor 22 into a bore. When the anchor 22 shown in FIG. 24 is secured into a bore in a medium, the anchor is prevented from moving in either proximal or distal directions. In contrast, the anchor shown in the embodiment described with reference to FIGS. 6 and 9 prevents movement of the anchor proximally. However, in such an embodiment, it is assumed that forces tending to move the anchor in a distal direction will not be provided to the anchor or that even if provided, the anchor is disposed in a "blind" or "bottomed" hole, and thus is prevented from moving distally.

As will be appreciated by those of skill in the art, the anchor 22, central member 22A and shaft 66, if provided as a suture anchor, are made of a suitable biocompatible material, e.g., metal or plastic. The remainder of the instrument can be made of suitable plastic or metal, as appropriate. Preferably, the entire tool, with anchor assembled thereon, is pre-packaged, preferably sterilized, as a unit for a single use. The insertion tool can, after implanting the anchor, be discarded. Or course, the device of the invention can also be employed reusably or recycled, after suitable sterilization, as appreciated by those of skill in the art.

Although the present invention has been described in relation to particular embodiments thereof, many other variations and modifications and other uses will become apparent to those skilled in the art. Therefore the present invention should be limited not by the specific disclosure herein, but only by the appended claims.

What is claimed is:

1. Apparatus for inserting an anchor into a bore in a medium, the anchor being adapted to engage the walls of the bore for securing the anchor into the medium, the apparatus comprising:

a first manually graspable member having a distal end, a proximal end and a longitudinal axis, the distal end being adapted to releasably receive an anchor, said manually graspable member having a central opening therethrough, the proximal end of the manually graspable member having a pivotable handle extending therefrom;

a second member movable longitudinally in the central opening attached to said pivotable handle and to said anchor;

a release member releasably coupling said anchor to said second member;

said pivotable handle being pivotable with respect to said first member about an axis perpendicular to the longitudinal axis of the first member and exerting a force longitudinally on said second member as said handle pivots to move said second member longitudinally in said first member and exert a force on said anchor connected thereto to deform said anchor to cause said anchor to engage the walls of the medium thereby to secure the anchor in the medium;

said longitudinal force exerted on said second member as said handle pivots further acting on said release member to separate said anchor from said second member after said anchor has deformed to engage the walls of the bore.

2. The apparatus of claim 1, wherein the apparatus is disposable and designed for a single use.

3. Apparatus for inserting an anchor into a bore in a medium, the anchor being adapted to engage the walls of the bore for securing the anchor into the medium, the apparatus comprising:

a first manually graspable member having a distal end and a proximal end, the distal end being adapted to releasably receive an anchor, said manually graspable member having a central opening therethrough, the proximal end of the manually graspable member having a pivotable handle extending therefrom;

a second member movable longitudinally in the central opening attached to said pivotable handle and to said anchor;

a release member releasably coupling said anchor to said second member;

said pivotable handle being pivotable with respect to said first member and exerting a force longitudinally on said second member as said handle pivots to move said second member longitudinally in said first member and exert a force on said anchor connected thereto to deform said anchor to cause said anchor to engage the walls of the medium thereby to secure the anchor in the medium;

said longitudinal force exerted on said second member as said handle pivots further acting on said release member to separate said anchor from said second member after said anchor has deformed to engage the walls of the bore; and wherein the release member coupling the anchor to the second member comprises a frangible connection which breaks upon the exertion of said force on said second member beyond a preset amount.

4. The apparatus of claim 3, wherein the second member comprises:

a flexible longitudinally extending member coupled to said handle; and a coupler fastened to a distal end of the flexible member, the coupler being attached to said anchor.

5. The apparatus of claim 4, wherein said flexible member comprises a wire or cable.

6. The apparatus of claim 4, wherein the anchor comprises:

a cylindrical hollow section having a plurality of longitudinally extending fingers for outward radial movement for engaging the walls of the bore on deformation of the anchor; and a central longitudinally extending member extending through the hollow section having a shoulder at a distal end preventing movement proximally past the hollow section, the central member having a shaft for engagement by the coupler, said central member including said frangible connection.

7. The apparatus of claim 6, wherein the central member is threaded into engagement with an internally threaded bore in said coupler.

8. The apparatus of claim 6, wherein said anchor comprises two cylindrical hollow sections each having a plurality of longitudinally extending interdigitated fingers, the fingers of one section extending proximally and the fingers of the other section extending distally.

9. The apparatus of claim 5, wherein the first member at the distal end thereof includes a surface for engaging one of said hollow sections, and each said section includes a cam surface for engaging an opposed one of said fingers on the opposite section for deforming said opposed fingers outwardly for engagement with the walls of the bore in the medium upon the application of said force to said second member.

10. The apparatus of claim 6, wherein the first member at the distal end thereof includes: a cam surface for engaging the fingers of said hollow section to deform said fingers outwardly for engagement with the walls of the bore in the medium upon the application of said force to said second member.

11. The apparatus of claim 6, wherein said anchor comprises a medical suture anchor for anchoring a suture in organic tissue, said first member including at least one opening therein through which a suture fastened to said anchor is threaded.

12. The apparatus of claim 11, wherein said central member has a forked end extending distally, said suture being looped through a region between forks of said forked end, the first member having two opposed openings therein through which respective free ends of the suture are threaded.

13. The apparatus of claim 11, wherein there are a plurality of sutures.

14. The apparatus of claim 6, wherein said frangible connection comprises a portion of reduced thickness and strength in said central member.

15. The apparatus of claim 14, wherein said hollow section and central member comprise metal or plastic.

16. The apparatus of claim 15, wherein said hollow section and central member comprise biocompatible metal or plastic.

17. The apparatus of claim 4, wherein said handle at the proximal end of the first member is fastened to said first member by a second frangible connection, said second frangible connection being breakable upon the application of a transverse force to said handle causing said handle to pivot with respect to said first member and exert the longitudinal force on said flexible member.

18. The apparatus of claim 17, wherein said handle includes a cam surface at a distal end for engaging with an opposed cam surface on the first member after said second frangible connection breaks, the engagement of said cam surfaces with each other upon application of said transverse force causing said flexible member to be pulled through said first member, causing said longitudinal force to be applied to said anchor to deform said anchor.

19. The apparatus of claim 18, wherein said handle, said second frangible connection and two opposed cam surfaces comprise an integral unit with the first member, the flexible member being slidably receivable in said first member.

20. The apparatus of claim 18, wherein said flexible member is secured in a coupling at said distal end thereof, said coupling being threadedly engaged in a passageway in said handle.

21. The apparatus of claim 17, wherein said second frangible connection comprises a portion of reduced thickness and strength in said handle.

22. The apparatus of claim 21, wherein the handle comprises a plastic.

23. The apparatus of claim 4, wherein the coupler is slidable in an insert received within the distal end of said first member.

24. A method of securing an anchor into a bore in a medium, the anchor being adapted to engage the walls of the bore for securing the anchor into the medium, the method comprising:

inserting an anchor held to a distal end of an insertion tool into the bore, the insertion tool having a longitudinal axis;

applying a force to a lever extending from the insertion tool to pivot the lever about an axis perpendicular to the longitudinal axis to cause a force to be exerted on the anchor by a coupling member to deform the anchor into engagement with the walls of the bore in the medium and separating the anchor from the coupling member; and pulling the insertion tool away from the anchor leaving the anchor secured in the bore in the medium.

25. A method of securing an anchor into a bore in a medium, the anchor being adapted to engage the walls of the bore for securing the anchor into the medium, the method comprising:

inserting an anchor held to a distal end of an insertion tool into the bore;

applying a force to a lever extending from the insertion tool to cause a force to be exerted on the anchor by a coupling member to deform the anchor into engagement with the walls of the bore in the medium and separating the anchor from the coupling member; and pulling the insertion tool away from the anchor leaving the anchor secured in the bore in the medium;

wherein the step of separating the anchor from the coupling member comprises breaking a frangible connection between the anchor and the coupling member by the application of said force after said anchor has deformed into engagement with the walls of said bore.

26. The method of claim 25, wherein the step of applying a force to the lever handle includes the step of breaking a frangible connection between the lever handle and the insertion tool and pivoting the handle about the insertion tool on opposed cam surfaces of the handle and insertion tool to apply said force to a flexible member coupled to the anchor to transfer the force to the anchor to deform the anchor and break the frangible connection between the anchor and the coupling member.

27. The method of claim 24, wherein the step of deforming the anchor comprises exerting said force on said anchor to pull proximally extending fingers of said anchor into engagement with a cam surface causing said fingers to extend radially outwardly into engagement with the walls of the bore.

28. The method of claim 27, wherein the anchor comprises proximal and distal hollow cylindrical sections having interdigitated longitudinally extending fingers and further wherein the step of deforming the anchor comprises exerting said force on said anchor to move proximally extending fingers on the distal hollow cylindrical section and distally extending fingers on the proximal hollow cylindrical section into engagement with opposed cam surfaces on the opposite hollow cylindrical section causing said fingers to extend radially outwardly into engagement with the walls of the bore.

29. A method of securing an anchor into a bore in a medium, the anchor being adapted to engage the walls of the bore for securing the anchor into the medium, the method comprising:

inserting an anchor, connected to a coupling member held to a distal end of an insertion tool, into the bore;

applying a force to a lever extending from the insertion tool to cause a force to be exerted on the anchor by a coupling member to deform the anchor into engagement with the walls of the bore in the medium and separating the anchor from the coupling member; and pulling the insertion tool away from the anchor leaving the anchor secured in the bore in the medium;

wherein said anchor comprises a biocompatible anchor adapted to be implanted in organic tissue and further comprising the step of coupling a suture to said anchor prior to said step of inserting.

30. A method of securing an anchor into a bore in a medium, the anchor being adapted to engage the walls of the bore for securing the anchor into the medium, the method comprising:

inserting an anchor held to a distal end of an insertion tool into the bore;

applying a force to a lever extending from the insertion tool to cause a force to be exerted on the anchor by a coupling member to deform the anchor into engagement with the walls of the bore in the medium and separating the anchor from the coupling member; and pulling the insertion tool away from the anchor leaving the anchor secured in the bore in the medium;

wherein the step of applying a force to the lever comprises applying a transverse force to the lever to cause the lever to pivot and cam against a surface of the insertion tool thereby to apply a tensile force to the coupling member.

31. Apparatus for inserting an anchor into a bore in a medium, the anchor being adapted to engage the walls of the bore for securing the anchor into the medium, the apparatus comprising:

an anchor comprising at least one hollow cylindrical section having longitudinally extending fingers adapted to be deformed radially outwardly to engage the walls of the bore to secure the anchor in the medium;

a first manually graspable member having a distal end, a proximal end and a longitudinal axis, the distal end releasably receiving the anchor, said manually graspable member having a central opening therethrough, the proximal end of the manually graspable member having a pivotable handle extending therefrom;

a second member movable longitudinally in the central opening attached to said pivotable handle and to said anchor;

a release member releasably coupling said anchor to said second member;

said pivotable handle being pivotable with respect to said first handle about an axis perpendicular to the longitudinal axis of the first member and exerting a force longitudinally on said second member as said handle pivots to move said second member longitudinally in said first member and exert a force on said anchor connected thereto to deform said anchor to cause said anchor to engage the walls of the medium thereby to secure the anchor in the medium; and said longitudinal force exerted on said second member as said member pivots further acting on said release member to separate said anchor from said second member after said anchor has deformed to engage the walls of the bore.

32. The apparatus of claim 31, wherein the apparatus is disposable and designed for a single use.

33. Apparatus for inserting an anchor into a bore in a medium, the anchor being adapted to engage the walls of the bore for securing the anchor into the medium, the apparatus comprising:

an anchor comprising at least one hollow cylindrical section having longitudinally extending fingers adapted to be deformed radially outwardly to engage the walls of the bore to secure the anchor in the medium;

a first manually graspable member having a distal end and a proximal end, the distal end releasably receiving the anchor, said manually graspable member having a central opening therethrough, the proximal end of the manually graspable member having a pivotable handle extending therefrom;

a second member movable longitudinally in the central opening attached to said pivotable handle and to said anchor;

a release member releasably coupling said anchor to said second member;

said pivotable handle being pivotable with respect to said first member and exerting a force longitudinally on said second member as said handle pivots to move said second member longitudinally in said first member and exert a force on said anchor connected thereto to deform said anchor to cause said anchor to engage the walls of the medium thereby to secure the anchor in the medium; and said longitudinal force exerted on said second member as said pivots further acting on said release member to separate said anchor from said second member after said anchor has deformed to engage the walls of the bore;

wherein the release member coupling the anchor to the second member comprises a frangible connection which breaks upon the exertion of said force on said second member beyond a preset amount.

34. The apparatus of claim 33, wherein the second member comprises:

a flexible longitudinally extending member coupled to said handle; and a coupler fastened to a distal end of the flexible member, the coupler being attached to said anchor.

35. The apparatus of claim 34, wherein said flexible member comprises a wire or cable.

36. The apparatus of claim 34, wherein the coupler is slidable in an insert received within the distal end of said first member.

37. The apparatus of claim 34, wherein said handle at the proximal end of the first member is fastened to said first member by a second frangible connection, said second frangible connection being breakable upon the application of a transverse force to said handle causing said handle to pivot with respect to said first member and exert the longitudinal force on said flexible member.

38. The apparatus of claim 37, wherein said handle includes a cam surface at a distal end for engaging with an opposed cam surface on the first member after said second frangible connection breaks, the engagement of said cam surfaces with each other upon application of said transverse force causing said flexible member to be pulled through said first member, causing said longitudinal force to be applied to said anchor to deform said anchor.

39. The apparatus of claim 38, wherein said handle, said second frangible connection and two opposed cam surfaces comprise an integral unit with the first member, the flexible member being slidably receivable in said first member.

40. The apparatus of claim 38, wherein said flexible member is secured in a coupling at said distal end thereof, said coupling being threadedly engaged in a passageway in said handle.

41. The apparatus of claim 37, wherein said second frangible connection comprises a portion of reduced thickness and strength in said handle.

42. The apparatus of claim 41, wherein the handle comprises a plastic.

43. The apparatus of claim 33, wherein the anchor comprises:

said cylindrical hollow section having a plurality of longitudinally extending fingers for outward radial movement for engaging the walls of the bore on deformation of the anchor; and a central longitudinally extending member extending through the hollow section having a shoulder at a distal end preventing movement proximally past the hollow section, the central member having a shaft for engagement by the coupler, said central member including said frangible connection.

44. The apparatus of claim 43, wherein the central member is threaded into engagement with an internally threaded bore in said coupler.

45. The apparatus of claim 43, wherein said anchor comprises two cylindrical hollow sections each having a plurality of longitudinally extending interdigitated fingers, the fingers of one section extending proximally and the fingers of the other section extending distally.

46. The apparatus of claim 45, wherein the first member at the distal end thereof includes a surface for engaging one of said hollow sections, and each said hollow section includes a cam surface for engaging opposed ones of said fingers on the opposite section for deforming said opposed fingers outwardly for engagement with the walls of the bore in the medium upon the application of said force to said second member.

47. The apparatus of claim 43, wherein the first member at the distal end thereof includes: a cam surface for engaging the fingers of said hollow section to deform said fingers outwardly for engagement with the walls of the bore in the medium upon the application of said force to said second member.

48. The apparatus of claim 43, wherein said anchor comprises a medical suture anchor for anchoring a suture in organic tissue, said first member including at least one opening therein through which a suture fastened to said anchor is threaded.

49. The apparatus of claim 48, wherein said central member has a forked end extending distally, said suture being looped through a region between forks of said forked end, the first member having two opposed openings therein through which respective free ends of the suture are threaded.

50. The apparatus of claim 48, wherein there are a plurality of sutures.

51. The apparatus of claim 43, wherein said frangible connection comprises a portion of reduced thickness and strength in said central member.

52. The apparatus of claim 51, wherein said hollow section and central member comprise metal or plastic.

53. The apparatus of claim 52, wherein said hollow section and central member comprise a biocompatible metal or plastic.

54. An anchor for implantation in a bore in a medium, the anchor comprising:

a cylindrical hollow section having a plurality of longitudinally extending fingers for outward radial movement for engaging the walls of the bore in response to a force applied to the anchor by an insertion tool causing the fingers to move against a cam surface; and a central longitudinally extending member extending through the hollow section and having a shoulder at a distal end preventing movement proximally past the section, the central member having a shaft for engagement by an insertion tool, said central member including a releasable connection for separating a distal portion of the central member from a proximal portion of the central member coupled to the insertion tool;

the releasable connection comprising a frangible connection which breaks upon the exertion of a force by the insertion tool on the central member beyond a preset amount.

55. The anchor of claim 54, wherein said anchor comprises two cylindrical hollow sections each having a plurality of longitudinally extending interdigitated fingers, the fingers of one section extending proximally and the fingers of the other section extending distally.

56. The anchor of claim 54, wherein the frangible connection comprises a portion of reduced thickness and strength in said central member.

57. The anchor of claim 56, wherein the frangible connection comprises a slit or score line in the central member causing the central member to have reduced tensile strength at the slit or score line.

58. The anchor of claim 54, wherein the central member is threaded into engagement with an internally threaded bore of a coupler of an insertion tool.

59. The anchor of claim 54 wherein the hollow section and central member comprise metal or plastic.

60. The anchor of claim 59, wherein the hollow section and central member comprise biocompatible metal or plastic.

61. In combination with an insertion tool for installing an anchor in a bore in a medium, the anchor comprising:

a cylindrical hollow section having a plurality of longitudinally extending fingers for outward radial movement for engaging the walls of the bore in response to a force applied to the anchor by an insertion tool causing the fingers to move against a cam surface; and a central longitudinally extending member extending through the hollow section and having a shoulder at a distal end preventing movement proximally past the section, the central member having a shaft for engagement by an insertion tool, said central member including a releasable connection for separating a distal portion of the central member from a proximal portion of the central member coupled to the insertion tool; and wherein the insertion tool at a distal end thereof includes a cam surface for engaging the fingers of said hollow section to deform said fingers outwardly for engagement with the walls of the bore in the medium upon application of a force by said insertion tool.

62. The anchor of claim 55, further in combination with an insertion tool for installing the anchor;

wherein the insertion tool at a distal end thereof includes a surface for engaging one of said sections, and each said section includes a cam surface for engaging opposed ones of said fingers on the opposite section for deforming said opposed fingers outwardly for engagement with the walls of the bore in the medium upon the application of a force by said insertion tool.

63. In combination with an insertion tool for installing an anchor in a bore in a medium, the anchor comprising:

a cylindrical hollow section having a plurality of longitudinally extending fingers for outward radial movement for engaging the walls of the bore in response to a force applied to the anchor by an insertion tool causing the fingers to move against a cam surface; and a central longitudinally extending member extending through the hollow section and having a shoulder at a distal end preventing movement proximally past the section, the central member having a shaft for engagement by an insertion tool, said central member including a releasable connection for separating a distal portion of the central member from a proximal portion of the central member coupled to the insertion tool; and wherein said anchor comprises a medical suture anchor for anchoring a suture in organic tissue, the insertion tool having at least one opening therein through which the suture fastened to the anchor is threaded.

64. The anchor of claim 63 wherein there are a plurality of sutures.

65. In combination with an insertion tool for installing an anchor in a bore in a medium, the anchor comprising:

a cylindrical hollow section having a plurality of longitudinally extending fingers for outward radial movement for engaging the walls of the bore in response to a force applied to the anchor by an insertion tool causing the fingers to move against a cam surface; and a central longitudinally extending member extending through the hollow section and having a shoulder at a distal end preventing movement proximally past the section, the central member having a shaft for engagement by an insertion tool, said central member including a releasable connection for separating a distal portion of the central member from a proximal portion of the central member coupled to the insertion tool; and wherein said anchor comprises a medical suture anchor for anchoring a suture in organic tissue, the insertion tool having at least one opening therein through which the suture fastened to the anchor is threaded; and further wherein said central member has a forked end extending distally, said suture being looped through a region between forks of said forked end, the insertion tool having two opposed openings therein through which respective free ends of the suture are threaded.

* * * * *